United States Patent [19]
Hasebe et al.

[11] Patent Number: 6,034,035
[45] Date of Patent: Mar. 7, 2000

[54] LIQUID COMPOSITION FOR STABILIZING BIPYRIDINUM SERIES HERBICIDES

[75] Inventors: Keiko Hasebe; Tadayuki Suzuki; Yuichi Hioki, all of Wakayama, Japan

[73] Assignee: Kao Corporation, Tokyo, Japan

[21] Appl. No.: 08/793,691

[22] PCT Filed: Jun. 27, 1996

[86] PCT No.: PCT/JP96/01780

§ 371 Date: Feb. 27, 1997

§ 102(e) Date: Feb. 27, 1997

[87] PCT Pub. No.: WO97/01276

PCT Pub. Date: Jan. 16, 1997

[30] Foreign Application Priority Data

Jun. 27, 1995 [JP] Japan ..................... 7-161279

[51] Int. Cl.$^7$ .......... A01N 43/40; A01N 43/60; A01N 37/04; A01N 25/30
[52] U.S. Cl. .......... 504/136; 504/130; 504/142; 504/235; 504/244; 504/250; 504/251; 504/320; 71/DIG. 1; 71/DIG. 2
[58] Field of Search .................... 504/250, 235, 504/244, 251, 130, 136, 142, 320; 71/DIG. 1, DIG. 2

[56] References Cited

FOREIGN PATENT DOCUMENTS

| | | |
|---|---|---|
| 63-145205 | 6/1988 | Japan . |
| 63-284106 | 11/1988 | Japan . |
| 2-295907 | 12/1990 | Japan . |
| 4-211002 | 8/1992 | Japan . |
| 1306647 | 2/1973 | United Kingdom . |
| 92-12637 | 8/1992 | WIPO . |
| 95/17817 | 6/1995 | WIPO . |
| 95/31903 | 11/1995 | WIPO . |

OTHER PUBLICATIONS

Turner, D.J. et al., "Complexing Agents as Herbicide Additives," Weed Research, vol. 18, 1978, pp. 199–207.
Chemical Abstracts 86:84676 (1977).
Chemical Abstracts 67: 20913 (1967).
Chemical Abstracts 76: 122968 (1971).

*Primary Examiner*—John Pak
*Attorney, Agent, or Firm*—Birch, Stewart, Kolasch & Birch, LLP

[57] ABSTRACT

A liquid enhancer composition for bipyridinium series herbicides comprising specific tertiary amine and a derivative thereof, at least one oxalic acid or a salt thereof selected from the group consisting of oxalic acid, potassium oxalate, alkanolamine salts of oxalic acid, and lower alkylamine salts of oxalic acid, wherein the ratio of oxalic acid or the salt thereof is 0.1 to 10 times mole per mole of the nitrogen-containing compound. The enhancer composition of the present invention has an excellent stability with lapse of time to a change in temperatures and can markedly enhance the medicinal efficacy of an bipyridinium series herbicide even when the composition is used in a liquid form in combination with the herbicide.

6 Claims, No Drawings

LIQUID COMPOSITION FOR STABILIZING BIPYRIDINUM SERIES HERBICIDES

This application is a 371 of PCT/JP96/01780, filed on Jun. 27, 1996.

FIELD OF THE INVENTION

The present invention relates to an enhancer composition for agricultural chemicals and an agricultural chemical composition containing the same, more specifically to a liquid enhancer for herbicides having a higher enhancer effect to bipyridinium series herbicides, which is represented by paraquat, and an excellent storage stability.

RELATED ART

Agricultural chemicals including insecticides, fungicides, herbicides, miticides, and plant growth regulators have been used in the forms of emulsions, wettable powder, granules, powder materials, and flowables. In using them, various attempts in terms of the properties of the formulations have been made in order to fully bring out the effectivenesses of agricultural chemical components. However, the existing situation is that it is difficult to further enhance the effectivenesses of agricultural chemicals through contrivances in terms of formulations. It is further difficult to develop novel agricultural chemicals, so that it is industrially very significant to further enhance the activities of existing agricultural chemicals.

As substances having the effect of enhancing the activities of agricultural chemicals, surfactants comprising various nitrogen-containing compounds such as quaternary ammonium salts, betaines, and amine oxides have so far been known (JP-A-63-145205). It is known as well that among them, quaternized or further polyoxyethylenated long-chain amines are particularly effective (JP-A-4-211002, JP-A-2-295907, and JP-A-63-284106). However, the medicinal efficacy-enhancing effects of these compounds are not necessarily satisfactory, and a further improvement in the effect has been desired. Accordingly, in order to meet such the desire, the present inventors have proposed to use quaternary ammonium salts or tertiary amines or salts thereof in combination with chelating agents, as shown in WO95/17817 published in English on Jul. 6, 1995 corresponding to Japanese Patent Application No. 5-337502 filed on Dec. 28, 1993. In addition, WO92/12637 published Aug. 6, 1992 discloses a composition comprising glyphosate, an acid acceptor and a surfactant.

However, further investigations have resulted in clarifying that while this enhancer for agricultural chemicals shows marked enhancer effect to various agricultural chemicals, it is inferior in storage stability, particularly stability to a change in temperatures when it is stored in a liquid form over a long period of time. It has been clarified that this problem is serious particularly when using it in combination with bipyridinium series herbicides and the medicinal efficacies of bipyridinium series herbicides can not sufficiently be enhanced in some cases. Accordingly, it has become clear that such problems as described above have to be further improved.

DISCLOSURE OF THE INVENTION

Intensive researches made by the present inventors in order to obtain an enhancer for bipyridinium series herbicides which has a good stability to a change in temperatures even when it is stored in a liquid form over an extended period of time have resulted in finding that the intended liquid enhancer and liquid herbicide composition can be obtained by using a nitrogen-containing compound comprising specific tertiary amine and a derivative thereof in combination with oxalic acid or a specific oxalic acid salt, and thus completing the present invention.

That is, the present invention provides a liquid enhancer composition for bipyridinium series herbicides characterized by containing (1) at least one nitrogen-containing compound selected from tertiary amines represented by the following Formula (1) and derivatives thereof, and (2) at least one oxalic acid or salt thereof selected from the group consisting of oxalic acid, potassium oxalate, alkanolamine salts of oxalic acid, and lower alkylamine salts of oxalic acid, wherein the content of oxalic acid or a salt thereof is 0.1 to 10 times mole per mole of the nitrogen-containing compound described above:

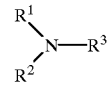

(1)

[wherein
R$^1$: represents a linear or branched alkyl group having a carbon number of 8 to 30 or a linear or branched alkenyl group having a carbon number of 8 to 30, and
R$^2$, R$^3$: may be the same as or different from each other and each represent a linear or branched alkyl group having a carbon number of 1 to 30, a linear or branched alkenyl group having a carbon number of 2 to 30, or —(AO)$_n$—H (AO is an oxyalkylene group having a carbon number of 2 to 4, and n is a number of 1 to 30 on the average.]

The invention provides, in other words, a liquid enhancer composition for herbicides of bipyridinium compounds which comprises, or consisting essentially of, (1) at least one nitrogen-containing compound as above defined and (2) at least one oxalic acid compound as above defined, optionally further comprising a surfactant.

It is preferable that the derivative is selected from the group consisting of amine salts, quaternized products, betaines and amine oxides of the tertiary amine compound represented by Formula (1).

The composition may be in the form of an aqueous solution thereof, comprising 10 to 30 percent by weight of the nitrogen-containing compound.

An herbicide composition of the invention comprises (i) an effective amount of at least one nitrogen-containing compound as defined above and an effective amount of the oxalic acid compound as defined above and (ii) a herbicide of bipyridinium compound, a weight ratio of (i) to (ii) ranging from 0.05/1 to 50/1.

The invention moreover provides a method for enhancing the herbicidal effectiveness of (ii) a herbicide of bipyridinium compound with (i) an effective amount of at least one nitrogen-containing compound as defined above and an effective amount of the oxalic acid compound as defined above.

The tertiary amine which is the nitrogen-containing compound used in the present invention is represented by Formula (1) described above, wherein R$^1$ in Formula (1) is preferably a linear alkyl group or a linear alkenyl group having a carbon number of 8 to 20, more preferably an alkyl group or alkenyl group having a carbon number of 8 to 20, which is derived from natural oil and fat; when R$^2$ and R$^3$ are —(AO)$_n$—H, AO is preferably an oxyalkylene group having a carbon number of 2, and n is preferably a number of 1 to 10 on the average. To describe concretely, preferred examples of the tertiary amine include mono-long-chain alkylamine, for example, bis(2-hydroxyethyl)cocoamine, bis(2-hydroxyethyl)-tallowamine, bis(2-hydroxyethyl) oleylamine, and bis(2-hydroxyethyl)laurylamine. Further, included are polyoxyalkylenated long-chain alkylamine, for example, bis(polyoxyethylene(EOp=3 to 30))cocoamine, bis(pclyoxyethylene(EOp=3 to 30))tallowamine, bis (polyoxyethylene(EOp=3 to 30))oleylamine, bis (polyoxyethylene(EOp=3 to 30))laurylamine, bis (polyoxyethylene(EOp=3 to 30))palmstearylamine, bis (polyoxyethylene(EOp=3 to 10).polyoxypropylene(POp=3 to 10)]cocoamine, and bis(polyoxyethylene(EOp=3 to 10).polyoxypropylene(POp=3 to 10)]tallowamine. In the compounds described above, EOp represents an average addition mole number of ethylene oxide, and POp represents an average addition mole number of propylene oxide.

In the present invention, derivatives derived from the tertiary amine represented by Formula (1) described above can be used as well. The tertiary amine derivatives described above include amine salts, quaternized products, betaines, and amine oxides.

The tertiary amine salts include salts of inorganic acids such as hydrochloric acid and sulfuric acid, and salts of organic acids such as acetic acid. In particular, hydrochlorides and acetates are preferred.

The quaternized products of the tertiary amines described above can be obtained by using known quaternizing agents. The quaternizing agents include dialkylsulfuric acids (an alkyl group having a carbon number of 1 to 3) and halogenated alkyl (an alkyl group having a carbon number of 1 to 3, a benzyl group).

Products obtained from the tertiary amines described above are preferred as the quaternized products of the tertiary amines used in the present invention. To describe concretely, included are methyl chloride-quaternized products, benzyl chloride-quaternized products, dimethylsulfuric acid-quaternized products and diethylsulfuric acid quaternized products of the tertiary amines described above.

Further, the following quaternary ammonium salts are preferred as well:
(A) quaternized long-chain amines
  (a) tri-lower alkyl long-chain alkylaramonium chloride
    (i) trimethylcocoammonium (coco=C$_{12}$ to C$_{15}$ alkyl) chloride
    (ii) trimethyloctadecylammonium chloride
  (b) dialkyldli-lower alkylammonium chloride
    (i) dimethyldioctadecylammonium chloride
    (ii) dimethyldicocoalkylammonium chloride
(B) quaternized polyoxyalkylenated long-chain amines
  (a) alkyldi(polyoxyethylene)lower alkylammonium chloride
    (i) methylbis(omegahydroxypoly(oxyethylene)oleo) ammonium chloride in which polyoxyethylene is derived from 2 to 30 moles of ethylene oxides.

Betaines derived from the tertiary amines represented by Formula (1) include trialkylbetaine, to describe concretely, long-chain alkyldi-lower alkylbetaines such as lauryldimethylbetaine, stearyldimethylbetaine, cocodimethylbetaine, and decyldimethylbetaine.

The following products are suitable as amine oxide derived from the tertiary amine represented by Formula (1):
(A) trialkyla-mine oxide
  (i) lauryldimethylamine oxide
  (ii) stearyldimethylamine oxide
(B) dihydroxyethylalkylamine oxide
  (i) dihydroxyethyloctylamine oxide
  (ii) dihydroxyethyldodecylamine oxide
  (iii) dihydroxyethyltallowlamine oxide
(C) di(polyoxyethylene)alkylamine oxide
  (i) bis(polyoxyethylene)tallowamine oxide
  (ii) bis(polyoxyethylene)cocoamine oxide
  (iii) bis(polyoxyethylene)dodecylamine oxide
(D) lower alkylpolyoxyethylenealkylamine oxide
  (i) methylpolyoxyethylenecocoamine oxide.

In the present invention, the nitrogen-containing compound and oxalic acid or the specific oxalic acid salt as described above are used in combination. The salt of oxalic acid is potassium salt, alkanolamine salt, or lower alkylamine salt. The alkanolamine salt includes monoethanolamine salt, diethanolamine salt, and triethanolamine salt. The lower alkylamine salt includes monomethylamine salt, monoethylamine salt, dimethylamine salt, and diethylamine salt. The liquid enhancer composition which is stable to a change in temperatures can not be obtained from oxalic acid salts other than the above compounds. The oxalic acid salt is preferably potassium salt or alkanolamine salt, particularly preferably potassium salt or diethanolamine salt.

Oxalic acid or the salt thereof is used in a range of 0.1 to 10 moles, preferably 0.3 to 5 moles per mole of the nitrogen-containing compound. If the amount of oxalic acid or the salt thereof is less than 0.1 mole or exceeds 10 moles, the enhancement effect of bipyridinium series herbicides is deteriorated, and the composition becomes unstable to a change in temperatures.

In the liquid enhancer composition of the present invention, known surfactants can be used in combination.

Nonionic surfactants, anionic surfactants, and amphoteric surfactants, or the mixture thereof can be used as the surfactants capable of being used in combination.

These surfactants can be combined at the weight ratio of 1/1 to 1/10, preferably 1/2 to 1/6 based on the nitrogen-containing compound.

The nonionic surfactants include polyoxyethylene alkyl ether, polyoxyethylene alkylaryl ether, polyoxyethylene alkylaryl ether formaldehyde condensation product, polyoxyalkylene aryl ether, polyoxyalkylene alkyl ester, polyoxyalkylene alkylsorbitol ester, polyoxyalkylene sorbitan ester, polyoxyalkylene alkylglycerol ester, polyoxyalkylene block copolymer, polyoxyalkylene block copolymer alkylglycerol ester, polyoxyalkylene alkylsulfonamide, polyoxyalkylene rosin ester, polyoxypropylene block copolymer, polyoxyethylene oleyl ether, polyoxyalkylene alkylphenol, and the mixture of two or more kinds thereof.

Among the anionic surfactants, typical ones can be obtained in the form of an aqueous solution or a solid matter. The examples thereof include sodium mono- and di-alkylnaphthalenesulfonates, sodium alpha-olefinsulfonates, sodium alkanesulfonates, alkylsulfosuccinates, alkylsulfates, polyoxyalkylene alkyl ether sulfates, polyoxyalkylene alkylaryl ether sulfates, polyoxyalkylene styrylphenyl ether sulfates, mono- and di-alkylbenzenesulfonates, alkylnaphthalenesulfonates, formaldehyde condensation products of alkylnaphthalenesulfonates, alkyl diphenyl ether sulfonates, olefinic sulfonates, mono- and dialkylphosphates, polyoxyalkylene mono and dialkylphosphates, polyoxyalkylene mono and diphenyl ether phosphates, polyoxyalkylene mono and diaklylphenyl ether phosphates, polycarboxylates, fatty acid salts, linear and branched alkyl polyoxyalkylene ether acetic acid or the salts thereof, alkenyl polyoxyalkylene ether acetic acid or the salts thereof, stearic acid and the salts thereof, oleic acid and the salts thereof, N-methyl fatty acid taurides, and the mixtures of two or more kinds thereof (including sodium, potassium, ammonium and amine salts).

Among these surfactants, particularly preferred are the nonionic surfactants. Of them, preferred are ester types such as polyoxyalkylene sorbitan esters and polyoxyalkylene alkylglycerol esters, polyoxyalkylene alkyl ethers, and polyoxyalkylene alkylphenyl ethers.

The liquid enhancer composition for bipyridinium series herbicides of the present invention comprises the preceding nitrogen-containing compound, oxalic acid or the salt thereof, optional components blended according to necessity, and the balance of water. The form thereof is usually an aqueous solution. In the present invention, the nitrogen-containing compound is blended into the composition in a proportion of 10 to 30 weight %, preferably 15 to 25 weight %. The mole ratio of the oxalic acid (salt) nitrogen-containing compound has to be controlled to the ratio described previously.

Further, the present invention provides a liquid herbicide composition containing the liquid enhancer composition of the present invention and the bipyridinium series hebicide as described above.

The bipyridinium series herbicide includes, for example, paraquat (1,1'-dimethyl-4,4'-bipyridinium-dichloride), diquat (6,7-dihydrodipyrido[1,2-a:2',1'-c] pyrazinediium dibromide).

In the liquid herbicide composition of the present invention, the ratio of the enhancer composition of the present invention to the bipyridinium series herbicide is (i)/(ii)=0.05 to 50, preferably 0.05 to 20, and more preferably 0.1 to 10 in terms of a weight ratio of the total amount (i) of the nitrogen-containing compound and oxalic acid or the salt thereof contained in the enhancer composition to the agricultural chemical primary component (the active ingredient of the herbicide) (ii) contained in the bipyridinium series herbicide. The ratio of less than 0.05 can not sufficiently achieve the intended enhancement effect of the herbicide. Meanwhile, the ratio exceeding 50 does not allow further increase in the effect to be expected.

Further, pH regurators, inorganic salts, and thickeners may be added to the herbicide composition of the present invention according to necessity.

The pH regurator capable of being used in the present invention is citric acid, phosphoric acid (pyrophosphoric acid), gluconic acid, or the salts thereof.

The inorganic salts which can be used in the present invention include inorganic ammonium salts such as ammonium sulfate, ammonium nitrate, ammonium phosphate, ammonium thiocyanate, ammonium chloride, and ammonium sulfamate.

The formulation of the herbicide composition of the present invention is a single liquid type (single formulation type) containing the enhancer composition and the bipyridinium series herbicide. It can be used as well by mixing (diluting) the bipyridinium series herbicide or the aqueous solution thereof with the aqueous solution of the enhancer composition immediately before using in such a proportion that the agricultural chemical concentration of the herbicide becomes the desired value.

EXAMPLES

The present invention shall be explained below with reference to examples but shall not be restricted to these examples.

Example 1

The nitrogen-containing compounds and oxalic acid or the salts thereof shown in Table 1 were used to obtain various liquid enhancer compositions.

TABLE 1

| Composition No. | Nitrogen-containing compound | | Oxalic acid or salt thereof | | Mole* ratio | Water |
|---|---|---|---|---|---|---|
| 1 | Cocoalkyltrimethylammonium chloride | 20 g | Oxalic acid | 5.2 g | 1:0.75 | 74.8 g |
| 2 | Cocoalkyltrimethylammonium chloride | 20 g | Dipotassium oxalate | 9.6 g | 1:0.75 | 70.4 g |
| 3 | Cocoalkyltrimethylammonium chloride | 20 g | Disodium oxalate | 7.7 g | 1:0.75 | 72.3 g |
| 4 | Cocoalkyltrimethylammonium chloride | 20 g | Diammonium oxalate | 7.2 g | 1:0.75 | 72.8 g |
| 5 | Cocoalkyltrimethylammonium chloride | 20 g | Diethanolamine oxalate | 17.2 g | 1:0.75 | 62.8 g |
| 6 | Cocoalkyltrimethylammonium chloride | 20 g | Dimethylamine oxalate | 8.6 g | 1:0.75 | 71.4 g |
| 7 | POE(15)beef tallow amine | 20 g | Oxalic acid | 5.2 g | 1:3 | 74.8 g |
| 8 | POE(15)beef tallow amine | 20 g | Dipotassium oxalate | 9.6 g | 1:3 | 70.4 g |
| 9 | POE(15)beef tallow amine | 20 g | Disodium oxalate | 7.7 g | 1:3 | 72.3 g |
| 10 | POE(15)beef tallow amine | 20 g | Diammonium oxalate | 7.2 g | 1:3 | 72.8 g |
| 11 | POE(15)beef tallow amine | 20 g | Diethanolamine oxalate | 17.2 g | 1:3 | 62.8 g |
| 12 | POE(15)beef tallow amine | 20 g | Dimethylamine oxalate | 8.6 g | 1:3 | 71.4 g |
| 13 | POE(15)cocoalkylmonomethylammonium chloride | 20 g | Oxalic acid | 5.2 g | 1:3 | 74.8 g |
| 14 | POE(15)cocoalkylmonomethylammonium chloride | 20 g | Dipotassium oxalate | 9.6 g | 1:3 | 70.4 g |
| 15 | POE(15)cocoalkylmonomethylammonium chloride | 20 g | Disodium oxalate | 7.7 g | 1:3 | 72.3 g |
| 16 | POE(15)cocoalkylmonomethylammonium chloride | 20 g | Diammonium oxalate | 7.2 g | 1:3 | 72.8 g |
| 17 | POE(15)cocoalkylmonomethylammonium chloride | 20 g | Diethanolamine oxalate | 17.2 g | 1:3 | 62.8 g |
| 18 | POE(15)cocoalkylmonomethylammonium chloride | 20 g | Dimethylamine oxalate | 8.6 g | 1:3 | 71.4 g |
| 19 | POE(2)cocoalkylmonomethylammonium chloride POE(6)Lauryl ether | 4 g | Dipotassium oxalate | 9.6 g | 1:1.2 | 70.4 g |
| Comp. 1 | Cocoalkyltrimethylammonium chloride | 20 g | | | | 80 g |
| Comp. 2 | POE(15)beef tallow amine | 20 g | | | | 80 g |
| Comp. 3 | POE(15)cocoalkylmonomethylammonium chloride | 20 g | | | | 80 g |
| Comp. 4 | | | Dipotassium oxalate | 9.6 g | | 90.4 g |
| Comp. 5 | | | Diethanolamine oxalate | 17.2 g | | 82.8 g |

*Mole ratio . . . nitrogen-containing compound: oxalic acid or salt thereof

The structures of the respective nitrogen-containing compounds shown in Table 1 are as follows:

(1) Cocoalkyltrimethylammonium chloride

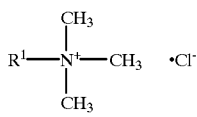

[R$^1$: cocoalkyl]

(2) POE (15) beef tallowamine

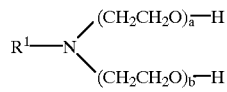

[R$^1$: beef tallowalkyl, a + b = 15 (average)]

(3) POE (15) cocoalkylmonomethylammonium chloride

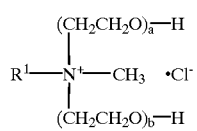

[R$^1$: cocoalkyl, a + b = 15 (average)]

(4) BisPOE (15) tallowamine oxide

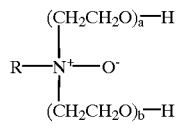

[R$^1$: tallowalkyl, a + b = 15 (average)]

BisPOE(15)tallowamine oxide of 20 g was used to prepare the liquid composition of total 100 g so that the mole ratio thereof to oxalic acid (salt) became 1:3, and the composition was evaluated in the same manner.

In order to confirm the stability with lapse of time of the compositions shown in Table 1, the compositions were stored at a high temperature (60° C.), a low temperature (−5° C.) and an ordinary temperature for one month. The results thereof are shown in Table 2.

TABLE 2

| Enhancer composition No. | Storage stability | | |
|---|---|---|---|
| | 60° C. | −5° C. | ord. temp. |
| 1 | stable | stable | stable |
| 2 | stable | stable | stable |
| 3 | s. & p. | c. & p. | p. |
| 4 | s. & p. | c. & p. | p. |
| 5 | stable | stable | stable |
| 6 | stable | stable | stable |
| 7 | stable | stable | stable |
| 8 | stable | stable | stable |
| 9 | s. & p. | c. & p. | p. |
| 10 | s. & p. | c. & p. | p. |
| 11 | stable | stable | stable |
| 12 | stable | stable | stable |
| 13 | stable | stable | stable |
| 14 | stable | stable | stable |
| 15 | s. & p. | c. & p. | p. |
| 16 | s. & p. | c. & p. | p. |
| 17 | stable | stable | stable |
| 18 | stable | stable | stable |
| 19 | stable | stable | stable |
| Comp. 1 | stable | stable | stable |
| Comp. 2 | stable | stable | stable |
| Comp. 3 | stable | stable | stable |
| Comp. 4 | stable | stable | stable |
| Comp. 5 | stable | stable | stable | s.; phase separation, p.; precipitation, c.; cloudiness

In Table, "stable": storage stability was good, and "precipitation, cloudiness and phase separation": change in physical properties such as precipitation, cloudiness, and phase separation was observed during a storage period of one month, and allowable storage stability was not shown.

As shown in Table 2, while the excellent temperature stability was shown when oxalic acid, dipotassium oxalate, diethanolamine oxalate, and dimethylamine oxalate were used, disodium oxalate and diammonium oxalate caused precipitates to be deposited after storing at a constant temperature for one month and therefore did not provide the stable liquid enhancer compositions which were allowable in terms of the stability with lapse of time.

The compositions using bisPOE(15)tallowamine oxide also provided good stability with lapse of time when they were used in combination with oxalic acid (salts) other than disodium oxalate or diammonium oxalate.

Example 2

The liquid enhancer compositions in Table 2 and combined with Priglox L liquid formulation (contain 7% by weight of diquat dibromide and 5% by weight of paraquat dichloride as an effective component) which is commercially available bipyridinium series herbicides to carry out a herbicidal efficacy test.

The liquid enhancer compositions each were dissolved in deionized water to obtain 1 to 500-diluted liquids. And the liquid enhancer compositions having bad stability during storage dissolved in deionized water to obtain 1 to 500-diluted liquids in the same manner. The resulting 1 to 500-diluted liquids of the liquid enhancer compositions were used to further dilute the Priglox L (trade name) liquid formulation described above to 1 to 500. Prigrox L is available from I.C.I. and Nippon Noyaku Co., Ltd.

Fertile soil obtained from a paddy field, gravel (that is, river sand), and commercially available culture soil were mixed together in a weight ratio 7:2:1. The soil thus obtained was put in pots having a inner diameter of 12 cm. In order to carry out a herbicidal efficacy test in a greenhouse, the seeds of crabgrass as an example of a narrow-leaved plant and cabbage as an example of a broad-leaved plant were sowed in the pots and grown. The pots in which the plants had been abnormally grown were removed in order to eliminate unevenness by pot. The pots in which crabgrass had grown to a grass height of 20 to 30 cm and cabbage leaves had grown up to a five leaves-spreading period were subjected to the test. In order to give the herbicide compositions to the plants, the pots were put on a turntable (diameter: 36 cm) to spray the compositions by means of a spray gun (RG type, manufactured by Iwata Tosoki Kogyo Co., Ltd.). The spray amount was adjusted to a ratio of 1000 liter/ha was sprayed evenly on the plants. Then, the herbicidal efficacies were evaluated.

The ground growth fresh weights were determined on the 14th day after spraying on the plants, and the results thereof were shown in terms of a herbicidal rate on the basis of the ground growth fresh weight of an untreated lot (refer to the following equation). Then, the herbicidal rates of the respective herbicide compositions are shown in Table 3.

Herbicidal rate (%)=[(ground growth fresh weight (g) of the untreated lot−ground growth fresh weight (g) of the treated lot)/ground growth fresh weight (g) of the untreated lot]×100

TABLE 3

| Enhancer composition No. | Herbicidal rate to crabgrass (%) | Herbicidal rate to cabbage (%) |
| --- | --- | --- |
| 1 | 85.6 | 66.7 |
| 2 | 83.2 | 65.8 |
| 3 | 73.5 | 50.8 |
| 4 | 75.1 | 53.6 |
| 5 | 81.8 | 62.1 |
| 6 | 84.1 | 63.4 |
| 7 | 91.5 | 70.3 |
| 8 | 92.6 | 72.4 |

TABLE 3-continued

| Enhancer composition No. | Herbicidal rate to crabgrass (%) | Herbicidal rate to cabbage (%) |
| --- | --- | --- |
| 9 | 74.8 | 54.3 |
| 10 | 76.2 | 56.5 |
| 11 | 84.6 | 68.3 |
| 12 | 85.2 | 65.0 |
| 13 | 90.4 | 73.8 |
| 14 | 88.9 | 74.0 |

TABLE 3-continued

| Enhancer composition No. | Herbicidal rate to crabgrass (%) | Herbicidal rate to cabbage (%) |
| --- | --- | --- |
| 15 | 74.2 | 57.9 |
| 16 | 72.4 | 56.5 |
| 17 | 84.3 | 88.5 |
| 18 | 84.3 | 70.3 |
| 19 | 87.5 | 72.3 |
| Comp. 1 | 74.2 | 52.6 |
| Comp. 2 | 75.8 | 54.3 |
| Comp. 3 | 75.2 | 50.6 |
| Non-additive | 70.3 | 40.6 |

In some cases, insoluble precipitation caused clogging of spray nozzle at spraying in the liquid enhancer compositions of No. 3, 4, 9, 10, 15, 16.

Among the compositions using bisPOE(15)tallowamine oxide, the compositions using oxalic acid (salt) other than disodium oxalate or diammonium oxalate showed a good herbicidal activity.

Example 3

Paraquat standard product and the liquid enhancer compositions for herbicides obtained in Example 1 were blended in the rates shown in Table 4, whereby the liquid herbicide compositions were obtained.

TABLE 4

| Herbicide composition | Enhancer composition for liquid herbicide | | Paraquat standard product (active ingredient 100%) | Water blend |
| --- | --- | --- | --- | --- |
| No. | No. | Blend amount (g) | blend amount (g) | amount (g) |
| (1) | 1 | 37.5 | 12.0 | 50.5 |
| (2) | 2 | 37.5 | 12.0 | 50.5 |
| (3) | 3 | 37.5 | 12.0 | 50.5 |
| (4) | 4 | 37.5 | 12.0 | 50.5 |
| (5) | 5 | 37.5 | 12.0 | 50.5 |
| (6) | 6 | 37.5 | 12.0 | 50.5 |
| (7) | 7 | 37.5 | 12.0 | 50.5 |
| (8) | 8 | 37.5 | 12.0 | 50.5 |
| (9) | 9 | 37.5 | 12.0 | 50 5 |
| (10) | 10 | 37.5 | 12.0 | 50.5 |
| (11) | 11 | 37.5 | 12.0 | 50.5 |
| (12) | 12 | 37.5 | 12.0 | 50.5 |
| (13) | 13 | 37.5 | 12.0 | 50.5 |
| (14) | 14 | 37.5 | 12.0 | 50.5 |
| (15) | 15 | 37.5 | 12.0 | 50.5 |
| (16) | 16 | 37.5 | 12.0 | 50.5 |
| (17) | 17 | 37.5 | 12.0 | 50.5 |
| (18) | 18 | 37.5 | 12.0 | 50.5 |
| (19) | 19 | 37.5 | 12.0 | 50.5 |
| (20) | Comp. 1 | 37.5 | 12.0 | 50.5 |
| (21) | Comp. 2 | 37.5 | 12.0 | 50.5 |
| (22) | Comp. 3 | 37.5 | 12.0 | 50.5 |
| (23) | Comp. 4 | 37.5 | 12.0 | 50.5 |
| (24) | Comp. 5 | 37.5 | 12.0 | 50.5 |

The liquid compositions using bisPOE(15)tallowamine oxide were prepared and evaluated in the same manners.

The herbicide compositions shown in Table 4 were stored at a high temperature (60° C.), a low temperature (−5° C.) and an ordinary temperature for one month in order to confirm the stability with lapse of time thereof. The results thereof are shown in Table 5.

TABLE 5

| Herbicide composition No. | Storage stability | | |
|---|---|---|---|
| | 60° C. | −5° C. | ord. temp. |
| 1 | stable | stable | stable |
| 2 | stable | stable | stable |
| 3 | s. & p. | c. & p. | c. & p. |
| 4 | s. & p. | c. & p. | c. & P. |
| 5 | stable | stable | stable |
| 6 | stable | stable | stable |
| 7 | stable | stable | stable |
| 8 | stable | stable | stable |
| 9 | s. & p. | c. & p. | c. & p. |
| 10 | s. & p. | c. & p. | c. & p. |
| 11 | stable | stable | stable |
| 12 | stable | stable | stable |
| 13 | stable | stable | stable |
| 14 | stable | stable | stable |
| 15 | s. & p. | c. & p. | c. & p. |
| 16 | s. & p. | c. & p. | c. & p. |
| 17 | stable | stable | stable |
| 18 | stable | stable | stable |
| 19 | stable | stable | stable |
| 20 | stable | stable | stable |
| 21 | stable | stable | stable |
| 22 | stable | stable | stable |
| 23 | stable | stable | stable |
| 24 | stable | stable | stable | s.; phase separation. p.; precipitation, c.; cloudiness

As shown in Table 5, the liquid herbicide compositions using the enhancers for liquid herbicides of the present invention were stable to a change in temperatures with lapse of time.

The compositions using bisPOE(15)tallowamine oxide provided a good storage stability as well.

Example 4

Various liquid herbicide compositions shown in Table 4 in Example 3 were used to carry out the following herbicidal efficacy test.

First, the liquid herbicide compositions each were diluted to 1 to 500 with deionized water to obtain spray liquids.

Fertile soil obtained from a paddy field, gravel (that is, river sand), and commercially available culture soil were mixed together in a weight ratio 7:2:1. The soil thus obtained was put in a pot having a inner diameter of 12 cm. In order to carry out the herbicidal efficacy test in a greenhouse, the seeds of crabgrass as an example of a narrow-leaved plant and cabbage as an example of a broad-leaved plant were sowed in the pots and grown. The pots in which the plants had been abnormally grown were removed in order to eliminate unevenness by pot. The pots in which crabgrass had grown to a grass height of 20 to 30 cm and cabbage leaves had grown up to a five leaves-spreading period were subjected to the test. In order to give the herbicide compositions to the plants, the pots were put on a turn table (diameter: 36 cm) to spray the compositions by means of a spray gun (RG type, manufactured by Iwata Tosoki Kogyo Co., Ltd.). The compositions were sprayed evenly on the plants in an amount corresponding to a ratio of 1000 liter/ha, and the herbicidal efficacies were evaluated.

The ground growth fresh weights were determined on the 14th day after spraying on the plants, and the results thereof were shown in terms of a herbicidal rate on the basis of the ground growth fresh weight of an untreated lot (refer to the following equation). The herbicidal rates of the respective herbicide compositions are shown in Table 6.

Herbicidal rate (%)=[(ground growth fresh weight (g) of the untreated lot−ground growth fresh weight (g) of the treated lot)/ground growth fresh weight (g) of the untreated lot]×100

TABLE 6

| Herbicide composition No. | Herbicidal rate to crabgrass (%) | Herbicidal rate to cabbage (%) |
|---|---|---|
| 1 | 83.4 | 63.2 |
| 2 | 81.5 | 65.0 |
| 3 | 70.3 | 40.6 |
| 4 | 71.6 | 42.5 |
| 5 | 80.9 | 60.4 |
| 6 | 82.6 | 62.9 |
| 7 | 89.7 | 69.1 |
| 8 | 87.6 | 70.6 |
| 9 | 72.1 | 44.5 |
| 10 | 70.1 | 42.6 |
| 11 | 82.3 | 65.5 |
| 12 | 80.9 | 63.3 |
| 13 | 88.6 | 72.5 |
| 14 | 87.5 | 71.8 |
| 15 | 69.8 | 40.8 |
| 16 | 72.2 | 42.5 |
| 17 | 81.5 | 67.1 |
| 18 | 81.6 | 68.9 |
| 19 | 86.5 | 72.0 |
| 20 | 67.5 | 40.3 |
| 21 | 70.2 | 41.4 |
| 22 | 68.5 | 42.5 |
| 23 | 54.6 | 32.7 |
| 24 | 57.2 | 35.4 |
| Priglox L liquid formulation | 69.8 | 41.2 |

In some cases, insoluble precipitation caused clogging of spray nozzle at spraying in the liquid enhancer compositions of No. 3, 4, 9, 10, 15, 16.

The compositions using bisPOE(15)tallowamine oxide showed a good herbicidal activiity as well.

We claim:

1. An herbicide composition comprising (i) an effective amount of (a) at least one nitrogen-containing compound as having the formula

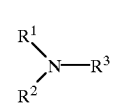

(1)

wherein
$R^1$ represents a Linear or branched alkyl group having the carbon number of 8 to 30 or a linear or branched alkenyl group having the carbon number of 8 to 30, and
$R^2$ and $R^3$ may be the same as or different from each other and each represent a linear or branched alkyl group having a carbon number of 1 to 30, a linear or branched alkenyl group having a carbon number of 2 to 30, or $-(AO)_n-H$ wherein AO is an oxyalkylene group having a carbon number of 2 to 4, and n is a number of 1 to 30 on the average; and (b) an effective amount of an oxalic acid compound selected from the group consisting of oxalic acid, potassium oxalate, and monoethanolamine, diethanolamine, triethanolamine, monomethylamine, monoethylamine, dimethylamine and diethylamine salts of oxalic acid, at a mole ratio of (b) to (a) of 0.1/1 to 10/1; and (ii) a bipyridinium herbicide compound selected from the group consisting of paraquat and diquat, or a mixture thereof.

2. The herbicide composition according to claim 1, wherein said oxalic acid compound is selected from the group consisting of dipotassium oxalate, diethanolamine oxalate, and dimethylamine oxalate.

3. The herbicide composition according to claim 1, wherein said nitrogen-containing compound is selected from the group consisting of cocoalkyltrimethylammonium chloride, POE(15) beef tallow amine, and POE(15) cocoalkylmonomethylammonium chloride.

4. A method for enhancing the herbicidal effectiveness of a bipyridinium herbicide compound selected from the group consisting of paraquat and diquat, or a mixture thereof which comprises applying (a) an effective amount of at least one nitrogen-containing compound

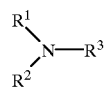
(1)

wherein
$R^1$ represents a linear or branched alkyl group having the carbon number of 8 to 30 or a linear or branched alkenyl group having the carbon number of 8 to 30, and $R^2$ and $R^3$ may be the same as or different from each other and each represent a linear or branched alkyl group having a carbon number of 1 to 30, a linear or branched alkenyl group having a carbon number of 2 to 30, or $-(AO)_n-H$ wherein AO is an oxyalkylene group having a carbon number of 2 to 4, and n is a number of 1 to 30 on the average; and (b) an effective amount of an oxalic acid compound selected from the group consisting of oxalic acid, potassium oxalate, and monoethanolamine, diethanolamine, triethanolamine, monomethylamine, monoethylamine, dimethylamine and diethylamine salts of oxalic acid, at a mole ratio of (b) to (a) of 0.1/1 to 10/1, with said herbicide to a locus in need of treatment.

5. The method according to claim 4, wherein said oxalic acid compound is selected from the group consisting of dipotassium oxalate, diethanolamine oxalate, and dimethylamine oxalate.

6. The method according to claim 4, wherein said nitrogen-containing compound is selected from the group consisting of cocoalkyltrimethylammonium chloride, POE(15) beef tallow amine, and POE(15) cocoalkylmonomethylammonium chloride.

* * * * *